(12) United States Patent
Kivatinos et al.

(10) Patent No.: US 11,417,417 B2
(45) Date of Patent: Aug. 16, 2022

(54) GENERATING CLINICAL FORMS

(71) Applicant: drchrono Inc., Sunnyvale, CA (US)

(72) Inventors: Daniel Kivatinos, Mountain View, CA (US); Michael Nusimow, Mountain View, CA (US); Martin Borgt, Sunnyvale, CA (US); Soham Waychal, Sunnyvale, CA (US)

(73) Assignee: DRCHRONO INC., Sunnyvale, CA (US)

( * ) Notice: Subject to any disclaimer, the term of this patent is extended or adjusted under 35 U.S.C. 154(b) by 684 days.

(21) Appl. No.: 16/457,803

(22) Filed: Jun. 28, 2019

(65) Prior Publication Data
US 2020/0035335 A1    Jan. 30, 2020

Related U.S. Application Data

(60) Provisional application No. 62/703,878, filed on Jul. 27, 2018.

(51) Int. Cl.
| | |
|---|---|
| *G16H 70/60* | (2018.01) |
| *G16H 50/20* | (2018.01) |
| *G16H 70/20* | (2018.01) |
| *A61B 5/11* | (2006.01) |
| *G16H 10/20* | (2018.01) |
| *G06N 3/04* | (2006.01) |
| *G06N 5/02* | (2006.01) |
| *G06K 9/62* | (2022.01) |
| *G06F 17/16* | (2006.01) |

(52) U.S. Cl.
CPC .............. *G16H 10/20* (2018.01); *G06F 17/16* (2013.01); *G06K 9/6215* (2013.01); *G06N 3/0454* (2013.01); *G06N 5/022* (2013.01); *G06N 5/027* (2013.01)

(58) Field of Classification Search
CPC ........ G16H 10/20; G16H 50/20; G06F 17/16; G06K 9/6215; G06N 3/0454; G06N 5/022; G06N 5/027; G06N 3/0445; G06N 3/084; G06V 10/82
USPC ...................................................... 706/1–62
See application file for complete search history.

(56) References Cited

U.S. PATENT DOCUMENTS

| | | | |
|---|---|---|---|
| 2006/0064017 A1* | 3/2006 | Krishnan .............. | G06T 7/0012 600/450 |
| 2017/0124263 A1* | 5/2017 | Crafts, Jr. ............. | G16H 70/20 |
| 2019/0340487 A1* | 11/2019 | Aggarwal .............. | G16H 70/60 |
| 2020/0034366 A1* | 1/2020 | Kivatinos ............. | G06K 9/6223 |
| 2020/0035335 A1* | 1/2020 | Kivatinos .............. | G06F 17/16 |
| 2020/0097814 A1* | 3/2020 | Devesa .................... | G06N 3/08 |

* cited by examiner

Primary Examiner — Brandon S Cole
(74) Attorney, Agent, or Firm — James J. DeCarlo; Greenberg Traurig, LLP

(57) ABSTRACT

A machine learning system may be used to predict clinical questions to ask on a clinical form. A first encoder may encode first information and a second encoder may encoder second information from a medical record of a past appointment. The first and second encoded information and additional encoded information may be used to predict a clinical question to ask by using a reinforcement learning system. The reinforcement learning system may be trained by receiving ratings of questions from users.

28 Claims, 4 Drawing Sheets

GENERATING CLINICAL FORMS

CROSS-REFERENCE TO RELATED APPLICATIONS

This application claims the benefit of U.S. Provisional Patent Application No. 62/703,878, filed Jul. 27, 2018, which is hereby incorporated by reference in its entirety.

FIELD OF THE INVENTION

The present invention relates to a computer system and method for using machine learning to automatically generate questions for a clinical form.

BACKGROUND

Health practitioners use a wide variety of forms in their practices. Many modern practice use forms on computer systems, which include one or more fields of information that may be saved to computer storage such as a database. Forms can be used for a variety of purposes such as intake, diagnosis, recording information from a patient examination and more. Some forms are completed by the patient and others are completed by the practitioner.

One problem that health practitioners face is not knowing the best questions to include on their forms. For example, it may be necessary to collect certain information in order to correctly diagnose the patient or to have the necessary information to submit a reimbursable insurance claim. The type of questions that should be asked on a form may depend on the specific situation. The best questions to ask may vary based on the patient, type appointment, type of practice, and other factors.

SUMMARY OF THE INVENTION

Some embodiments relate to a machine learning system for generating one or more clinical questions for a clinical form. The machine learning system may be used to suggest clinical questions based on feedback from users and based on information from a patient appointment. Clinical forms, or portions of clinical forms, may be generated by using the recommended clinical questions.

In one embodiment, a first encoder is trained to encode information of a first type into a first vector representation. A second encoder is trained to encode information of a second type into a second vector representation. More or fewer encoders may be used. A medical record from a past appointment of a patient may be provided. A first portion of information of the first type and a second portion of information of the second type may be extracted from the medical record. The first portion of information may be input to the first encoder to output first encoded information. The second portion of information may be input to the second encoder to output second encoded information. An aggregator may be used to aggregate first encoded information and second encoded information. A database of clinical questions may be provided. A prediction may be made of one or more clinical questions to ask from the database of clinical questions by using a reinforcement learning system. The reinforcement learning system may be trained by receiving ratings of questions from users.

In some embodiments, the encoders are implemented with neural networks. In some embodiments, the reinforcement learning system is implemented using Q-learning or Deep Q-learning.

DETAILED DESCRIPTION

Figure 1A:
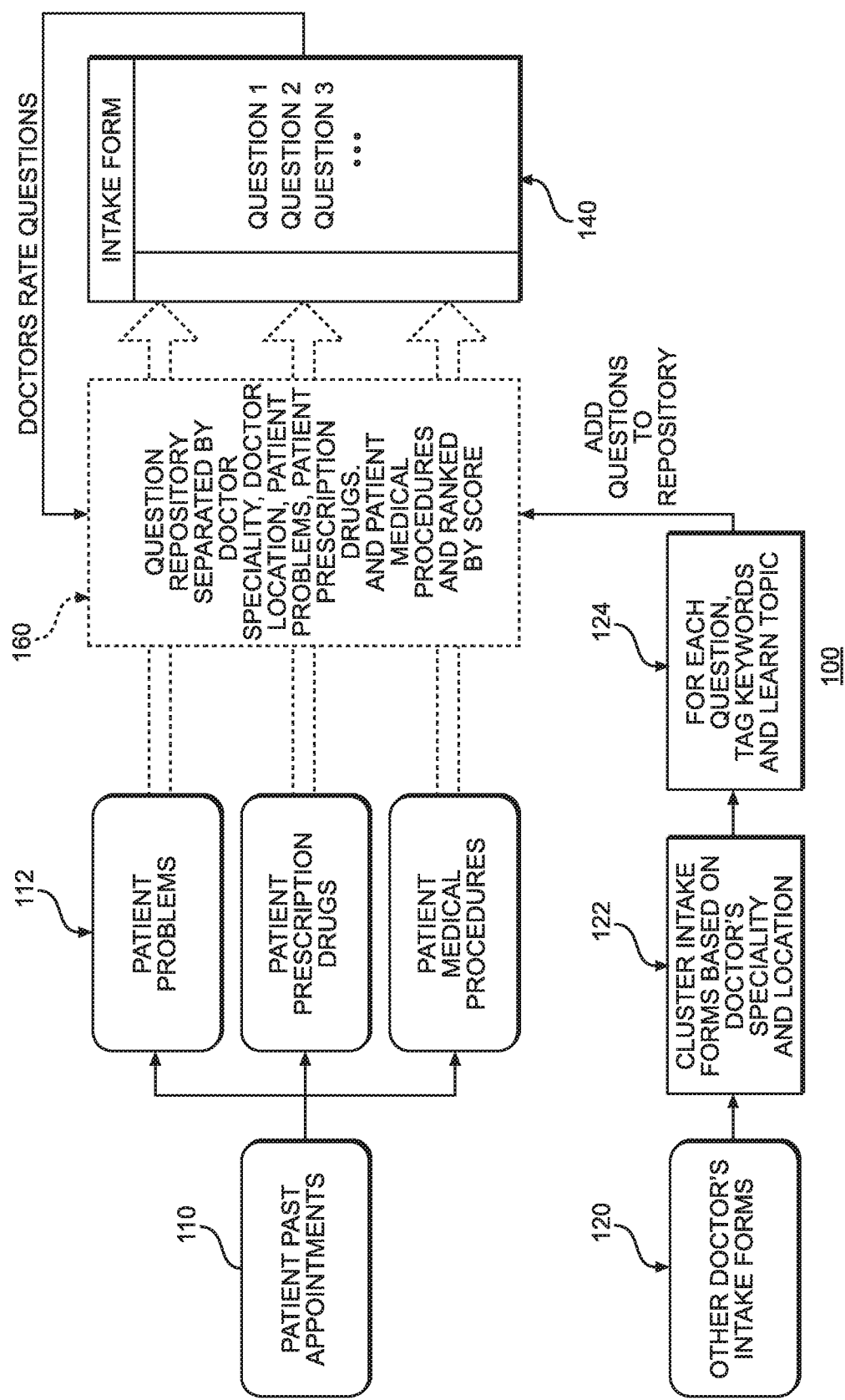
FIGS. 1A-B illustrate an exemplary question prediction system.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

FIG. 1A illustrates an exemplary question prediction system 100 consistent with some embodiments. The question prediction system 100 is implemented using computer software and hardware. The question prediction system 100 may comprise one computer system or multiple computer systems operating in coordination over a network or other communication channel.

Embodiments may be used to recommend questions for a clinical form. Clinical forms may include intake forms, forms for recording diagnoses, and forms for a practitioner to record information during a patient appointment or examination. Some clinical forms are completed by a patient and others are completed by a practitioner.

In question prediction system 100, other doctors' clinical forms 120 may be provided in electronic form, such as in the form of electronic templates, Microsoft Word Files, PDFs, or other formats. Clustering by a clustering algorithm, such as k-means clustering, may be used to cluster the other doctors' clinical forms based on various criteria, such as practitioner specialty and/or location (step 122). Questions may be tagged by keyword and the topics of the questions learned by computer analysis of the keywords (step 124). The questions may then be stored in a clinical question database 160, which serves as a repository of clinical questions. The clinical question database 160 may store metadata with each clinical question, such as keywords, topics, and associated specialties and locations.

When a new patient is presented at a practitioner's office, the question prediction system 100 may retrieve records of past appointments 110 for the patient from an electronic medical record system. The records of the past appointments 110 may include information about the past appointment, where the information may be of a plurality of types 112. Types of information 112 included in the records of past appointments 110 may include information about patient problems/diagnoses, medications, medical procedures, procedure codes, fee codes, billing codes, diagnosis codes, allergies, lab tests, reasons for the visit, prescribed drugs, patient vitals such as height and weight, and so on.

As an alternative to using records of past appointments 110, a summary of care may be used in the question prediction system 100. In some embodiments, the summary of care may be a C-CDA (Consolidated Clinical Document Architecture) file. The summary of care may include a summary of the care provided to a patient. In an embodiment, the summary of care may be generated when a patient is changing doctors, in order to provide a summary of the patient's care to the new doctor. A summary of care or records of past appointments 110 are both examples of electronic medical records.

Based on the information from electronic medical records of the patient, the question prediction system 100 may predict one or more clinical questions to ask from clinical question database 160. The predicted one or more clinical questions may be added to a clinical form 140, such as an intake form or other clinical form.

In some embodiments, the predicted clinical questions may be added to a clinical form without a notification that these clinical questions were automatically predicted. In other embodiments, an indicator may be displayed on the clinical form to identify the predicted clinical questions as automatically generated suggestions.

The user answering the question on the form, who may be a practitioner or a patient, may provide feedback on the predicted one or more predicted clinical questions may providing a rating. In some embodiments, the rating is on a scale of numbers, such as from 1 to 5. In some embodiments, the rating is a binary rating of good or bad. In some embodiments, the rating is not explicit but is inferred by the computer system based on whether the user answered the clinical question or left if blank, the amount of time it took the user to answer the question, the number of times the user changed their answer to the question, or other data.

In an embodiment, the question prediction system 100 predicts one or more questions to add to clinical form 140 before a patient's appointment. The predicted questions are displayed to a practitioner as recommendations when the practitioner opens the clinical form 140. If the practitioner accepts the recommendation and adds a predicted question to the form, then the question prediction system 100 provides the predicted question with a high rating. However, if the practitioner declines the recommendation and does not add the predicted question to the form, then the question prediction system 100 provides the predicted question with a low rating. Accordingly, the question prediction system 100 is trained based on which questions a practitioner decides to add, or declines to add, to a clinical form 140.

Figure 1B:
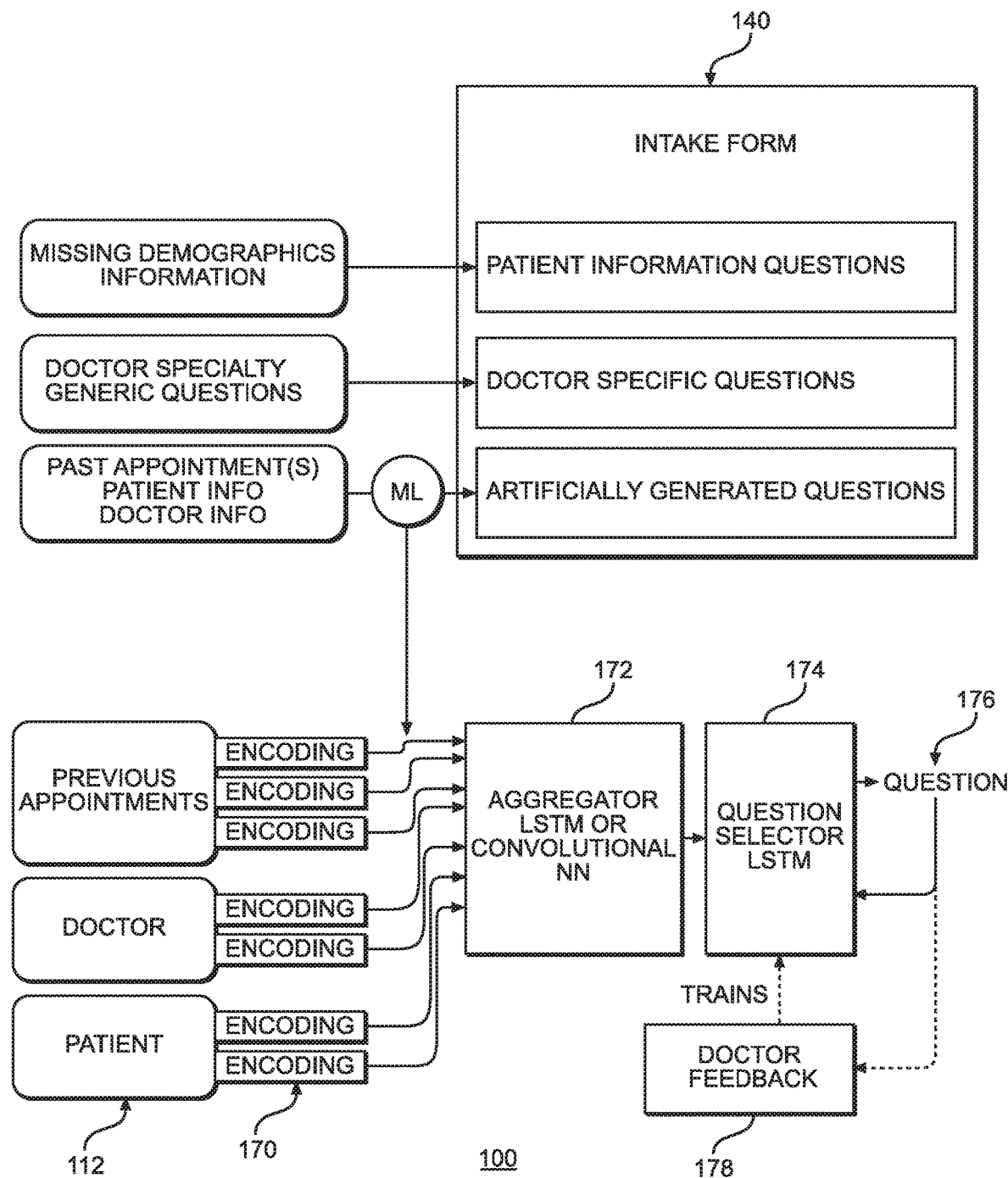

FIG. 1B illustrates a more detailed view of question prediction system 100. A clinical form 140 may include at least three different types of questions. First, the clinical form may include questions for patient information. This may include demographic and contact information such as email address, phone number, and so on. Second, the clinical form may include standard questions for the practitioner's practice type. For example, a question of this type may be "how much pain are you in on a scale of 1-10" for pain medication specialists. Third, the clinical form may include automatically generated questions based on patient data from electronic medical records. These questions may be automatically generated using machine learning.

In an embodiment, different types of information 112 may be identified and extract from electronic medical records of the patient. In an embodiment, the information 112 may include information from previous appointments; information about the practitioner, such as the practitioner's specialty and location; and information about the patient, such as age, gender, and other demographic information. Information 112 may include patient problems/diagnoses, medications, medical procedures, procedure codes, fee codes, billing codes, diagnosis codes, allergies, lab tests, reasons for the visit, prescribed drugs, patient vitals such as height and weight, and so on. These various pieces of information may be encoded into encodings 170.

In an embodiment, a neural network encoder is provided for each type of information to encode information of the type into a vector representation. A neural network encoder is an encoder that is implemented with one or more neural networks.

The encoding of an input to a vector representation may be used to relate inputs that are similar. For example, inputs that are similar may be mapped by the encoder to vectors that are close together in vector space, while inputs that are dissimilar may be mapped to vectors that are far apart in vector space. Vector distance may be measured by a number of metrics, such as cosine similarity or dot product.

One form of encoder that may be used for a neural network encoder is a neural network autoencoder. A neural network autoencoder is an autoencoder that is implemented with one or more neural networks. An autoencoder comprises an encoder and a decoder. The encoder accepts an input and outputs a vector representation. The decoder accepts the vector representation as input and outputs an output vector. The autoencoder is trained to produce an output vector that is the same as the input vector. The compression of the input vector to an intermediate vector representation means that the output vector may not be identical to the input vector. However, the training process for the autoencoder aims to reduce the vector distance between the output vector and the initial input to the encoder component of the autoencoder.

In an autoencoder, the intermediate vector representation between the encoder and decoder may be used as an encoding or embedding of the input. The vector representation commonly compresses the input to a lower-dimensional vector space.

A variational autoencoder is one type of autoencoder that may be used herein to implement the autoencoders. In a variational autoencoder, the Kullback-Leibler divergence may be used in the loss function for training the autoencoder. The loss function based on Kullback-Leibler divergence effectively encourages the encoder to distribute encodings evenly around the center of the vector space. The loss function penalizes the encoder if it attempts to cluster the encodings in specific regions, away from the origin.

As an alternative to a variational autoencoder, some embodiments may use a sequence-to-sequence (Seq2Seq) encoder-decoder. A Seq2Seq encoder-decoder includes a Seq2Seq encoder and Seq2Seq decoder. The Seq2Seq encoder treats codes as a sentence and encodes them together to create a concise encoding of the list of codes together. This allows encoding a sequence of inputs into a vector representation and mapping the vector representation back into a sequence using the Seq2Seq decoder. Seq2Seq encoders and decoders may be implemented with neural networks that map from sequences of inputs to a vector.

Such neural networks may include recurrent neural networks (RNNs) and long short-term memory (LSTM) neural networks. An LSTM is one form of RNN.

After the encodings 170 are generated, metadata may be added to each encoded representation to identify what type of information they encode, such as patient problems/diagnoses, medications, medical procedures, fee codes, billing codes, diagnosis codes, allergies, lab tests, and so on. In some embodiments, the metadata may be represented as one-hot vectors. A one-hot vector is a vector with a zero in all positions except for a single position with a one. The position of the one indicates the type of metadata. For example, the first position may indicate a diagnosis, the second position may indicate a medication, and so on. A one-hot vector identifying the type of information may be concatenated to each encoding. In some embodiments using metadata, a decoder to map from encoded representations back to regular inputs may take the form fWx where f is the metadata vector in one-hot format, W is a matrix with learned weights for performing decoding, and x is the encoded representation.

Regardless of how the encodings 170 are generated, they may be input to an aggregator 172. The aggregator 172 aggregates the encodings 170 into a single encoding that represents all of the relevant information about the patient, where the single encoding is, for example, a vector. Aggregation to a single encoding makes training the question selector 174 easier because the information about the patient has been summarized into a single representation. The aggregator 172 is a machine learning model such as RNN, LSTM, or convolutional neural network (CNN). The aggregator 172 is trained to output similar vector encodings when the clinical questions asked of the patients were similar, and to output dissimilar vector encodings when the clinical questions of the patients were different. Similarity between vectors may be evaluated using a distance metric like cosine similarity or the dot product.

In an embodiment, training examples are obtained by identifying patients who were asked similar or identical questions on the clinical form and using these as positive examples, and finding patients were not asked similar questions on the clinical form and using these as negative examples. Similarity between clinical questions may be measured by encoding the clinical questions using an encoder, such as a neural network encoder, and measuring vector distance, such as by cosine similarity or dot product. Vectors that are close are similar, and those that are far apart are dissimilar. The aggregator is trained to output a similar encoding for patients who were asked similar or identical questions and to output dissimilar encodings for patients who were not asked similar questions. In an embodiment, training is performed using the Triplet Loss Function. The Triplet Loss Function trains by using three examples: an anchor, a positive, and a negative. The Triplet Loss Function trains the anchor and the positive to have similar encodings, and trains the anchor and the negative to have different encodings.

In an embodiment, the aggregator 172 is implemented using an LSTM. The LSTM may be trained accept a variable length sequence of encodings 170 and output a hidden state. The hidden state of the LSTM after all of the encodings 170 have been input may comprise the output encoding of the aggregator 172. In the training process using the Triplet Loss Function, the encodings of the anchor example may be input into a first copy of the LSTM and the encodings of the positive may be input into a second copy of the LSTM. The resulting outputs may then be compared using the Triplet Loss Function, and backpropagation is applied to adjust the weights of the LSTM to make the outputs more similar. A similar process is applied for an anchor and a negative example, except that the Triplet Loss Function and backpropagation are applied to adjust the weights of the LSTM to make the output vectors farther apart.

In an embodiment, the aggregator 172 is implemented using a CNN. In a CNN, neural network nodes are connected in to neural network nodes in subsequent layers in only a local area around the node. That is, neural network nodes are not connected to other nodes that are far away from them in the subsequent layer. A CNN may have a plurality of layers that apply different convolutional kernels, also known as filters. In the training process using the Triplet Loss Function, the encodings of the anchor example may be input into a first copy of the CNN and the encodings of the positive may be input into a second copy of the CNN. The resulting outputs may then be compared using the Triplet Loss Function, and backpropagation is applied to adjust the weights of the CNN to make the outputs more similar. A similar process is applied for an anchor and a negative example, except that the Triplet Loss Function and backpropagation are applied to adjust the weights of the CNN to make the output vectors farther apart.

The encoding output by the aggregator 172 is input to the question selector 174 to enable the question selector 174 to predict question 176 for the clinical form 140. In an embodiment, the question selector 174 is implemented with a LSTM. The encoding output by the aggregator 172 is input as the initial hidden state of the LSTM 174. A start token is also input to the LSTM 174 to cause it to start producing outputs. The LSTM 174 iteratively produces new outputs and modifies the hidden state. Each output is a vector that represents an embedding of a question. A search is performed through clinical question database 160, which includes the questions and associated vectors representing the questions. The question selector 174 output vector is compared to these vectors to find the closest vector, and the associated question is selecting as the output question 176.

In an alternative, the question selector 174 may use an attention mechanism. The attention mechanism iteratively analyzes the input and scores how relevant each portion of the input is to the final output value. The attention model then selects the most relevant portions and uses them to predict the final output. In an embodiment, the attention model may iteratively analyze portions of the hidden state of the question selector 174 and identify the most relevant portions to process to produce the output question 176.

Regardless of the use of an LSTM or attention model, the question selector 174 may produce a question 176 or stop token at each iteration. If a stop token is reached, or a maximum number of questions is reached, then the question selector 174 may stop. Otherwise, the question selector may continue producing questions. In an embodiment, a minimum number of questions to produce is chosen, and the question selector 174 will continue producing questions until the minimum number of questions is reached even if a stop token has been produced. The question selector 174 may ignore the stop token and continue producing questions until another stop token is produced and the threshold number of questions has been produced.

In an embodiment, the question selector 174 is trained using reinforcement learning based on user feedback 178 on the question 176. Positive user feedback 178 for question 176 causes the internal weights of the question selector 174 to be adjusted to be more likely to produce the question 176 again. Negative user feedback 178 for question 176 causes the internal weights of the question selector 174 to be adjusted to be less likely to produce the question 176 again. Because it is trained using reinforcement learning, the question selector 174 comprises a reinforcement learning system.

In one embodiment, backpropagation is used for adjusting the internal weights of the question selector 174. When question 176 receives positive user feedback, backpropagation is used to adjust the internal weights to produce an output vector that is more similar, meaning closer in vector space, to vector representation of the nearest-neighbor question 176 that was output. When question 176 receives negative user feedback, backpropagation is used to adjust the internal weights to produce an output vector that is less similar, meaning farther in vector space, to the vector representation of the nearest-neighbor question 176 that was output.

Many different reinforcement learning approaches may be used for training the question selector 174. In some embodiments, the reinforcement learning system uses Q-learning. In an embodiment, a Q function is used to model the quality of each action in a state based on the expected total reward that will be achieved. The Q function may be modeled with a table or with a continuous function using function approximation. In some embodiments, the reinforcement learning system uses Deep Q-learning, which is Q-learning where the Q function is implemented using a deep neural network.

Figure 2A:
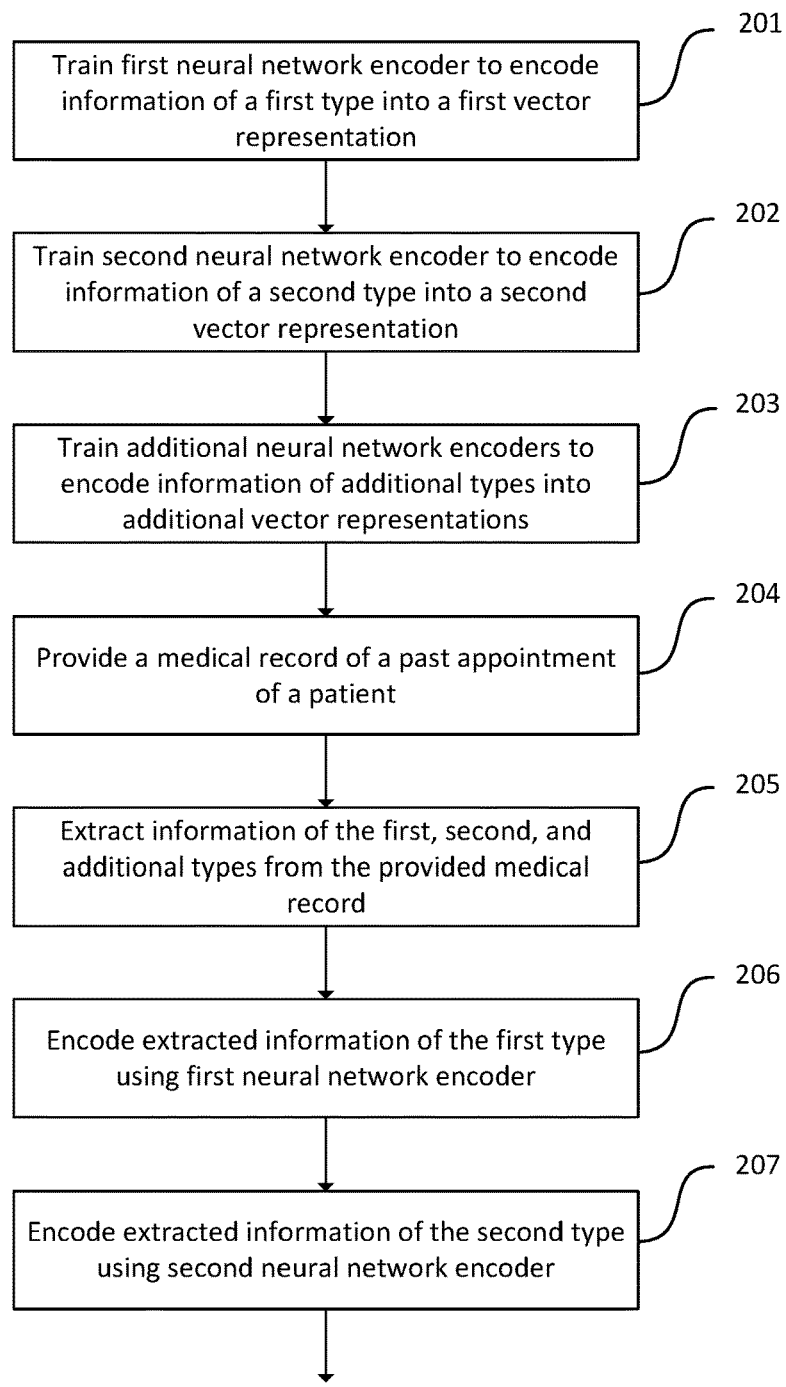
FIGS. 2A-B illustrate an exemplary method for predicting a clinical question to ask.
Figure 2B:
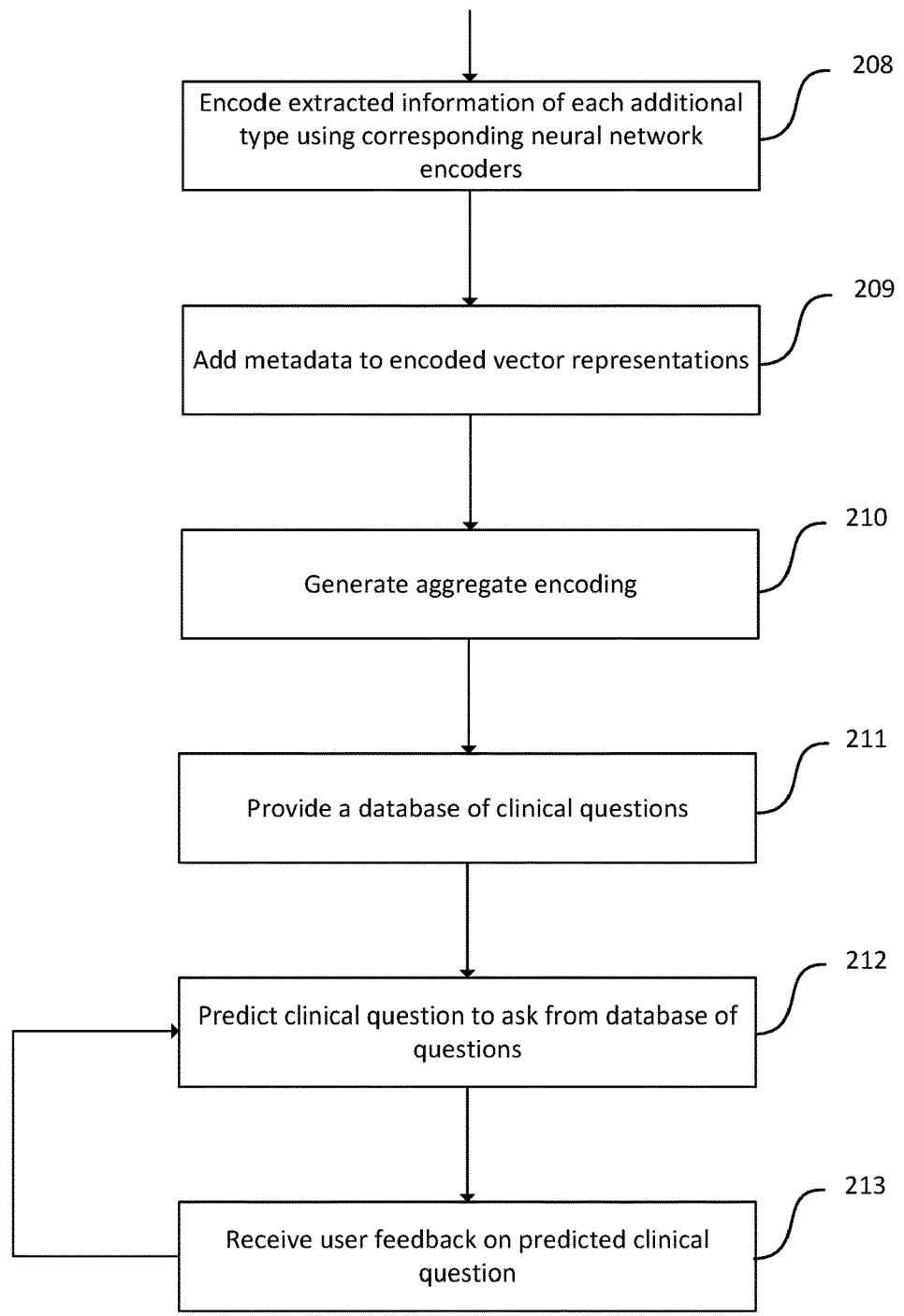

FIGS. 2A-B illustrate an exemplary method 200 for using question prediction system 100. In step 201, a first neural network encoder is trained to encode information of a first type into a first vector representation. This may be an autoencoder, variational autoencoder, Seq2Seq encoder-decoder, and so on.

In step 202, a second neural network encoder is trained to encode information of a second type into a second vector representation. This may be an autoencoder, variational autoencoder, Seq2Seq encoder-decoder, and so on.

In step 203, additional neural network encoders may be trained to encode information of additional types into vector representations. This process may continued for three, four, five, or more types of information until neural network encoders are trained to encode all of the desired information from electronic medical records. Typically a different neural network encoder will be used for each different type of information. For example, billing codes will be encoded by one neural network and diagnosis codes will be encoded by a separate neural network, and likewise for medications, lab tests, and so on.

In step 204, an electronic medical record of a patient is provided.

In step 205, a first portion of information of a first type and a second portion of information of a second type are extracted from the electronic medical record. An additional plurality of portions of information of other types may also be extracted from the medical record, such as a third information of a third type, fourth information of a fourth type, and so on.

In step 206, the first portion of information is input to the first neural network to output a first encoded representation.

In step 207, the second portion of information is input to the second neural network to output a second encoded representation.

In step 208, additional portions of information may be input to separate neural networks per type to output encoded representations of each portion of information.

In step 209, metadata may be added to each encoded representation, such as the first encoded representation, second encoded representation, and additional encoded representations, to identify what type of information they encode, such as patient problems/diagnoses, medications, medical procedures, fee codes, billing codes, diagnosis codes, allergies, lab tests, and so on.

In step 210, an aggregate encoding may be generated from the first encoded representation, second encoded representation, and additional encoded representations. In an embodiment, the first encoded representation, second encoded representation, and additional encoded representations are input to an aggregator machine learning system 172 to output the aggregate encoding.

In step 211, a database of clinical questions may be provided, where each question has an associated vector representation.

In step 212, a clinical question to ask from the database of clinical questions may be predicted based on the aggregate encoding. The aggregate encoding is input to a question selector 174. The question selector 174 processes the aggregate encoding to output an encoded output question. The encoded output question is compared to a set of vector representations of clinical questions in the database. The vector that is closest to the encoded output question is identified, and the associated clinical question is output as a predicted question.

In step 213, a rating of the predicted clinical question may be received from a user. The rating may be used for training the question selector 174 through a reinforcement learning process. The process may repeat at 212 to predict additional clinical questions.

In some embodiments, the method 200 may be performed for more than one past appointment of a patient so that recommended questions may be generated based on records of various different past appointments. In that case, the predicted clinical question that is presented may be the highest scoring of the clinical questions based on any of the past appointments. In some embodiments, the past appointments may be weighted by time with more recent appointments having higher weights than older appointments. The weights may be multiplied by the scores provided by the reinforcement learning system and the highest scoring clinical question may be chosen. This approach would give higher precedence to questions that derive from more recent appointments.

The terminology used herein is for the purpose of describing particular aspects only and is not intended to be limiting of the disclosure. As used herein, the singular forms "a," "an," and "the" are intended to comprise the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

While the invention has been particularly shown and described with reference to specific embodiments thereof, it should be understood that changes in the form and details of the disclosed embodiments may be made without departing from the scope of the invention. Although various advantages, aspects, and objects of the present invention have been discussed herein with reference to various embodiments, it will be understood that the scope of the invention should not be limited by reference to such advantages, aspects, and objects. Rather, the scope of the invention should be determined with reference to patent claims.

What is claimed:

1. A computer-implemented method for generating questions for a clinical form, the method comprising:
   training a first neural network autoencoder to encode information of a first type into a first vector representation, the first autoencoder comprising a first encoder that maps a first input vector to the first vector representation and a first decoder that maps the first vector representation to a first output vector, where the first decoder is trained to reduce the distance between the first output vector and the first input vector;
   training a second neural network autoencoder to encode information of a second type into a second vector representation, the second autoencoder comprising a second encoder that maps a second input vector to the second vector representation and a second decoder that maps the second vector representation to a second output vector, where the second decoder is trained to reduce the distance between the second output vector and the second input vector;
   providing a medical record of a past appointment of a patient;
   extracting from the medical record a first portion of information of the first type and a second portion of information of the second type;
   inputting the first portion of information to the first neural network autoencoder to output first encoded information;
   inputting the second portion of information to the second neural network autoencoder to output second encoded information;
   providing a database of clinical questions;
   inputting the first encoded information and second encoded information into a third neural network encoder to generate an aggregate encoding;
   predicting, by a question predictor, a clinical question to ask from the database of clinical questions based on the aggregate encoding.

2. The computer-implemented method of claim 1, wherein the first neural network autoencoder is a variational autoencoder.

3. The computer-implemented method of claim 1, wherein the first neural network autoencoder uses Kullback-Leibler divergence.

4. The computer-implemented method of claim 1, wherein the second neural network autoencoder is a variational autoencoder.

5. The computer-implemented method of claim 1, wherein the question predictor comprises a Q-learning system.

6. The computer-implemented method of claim 1, wherein the question predictor comprises a Deep Q-learning system.

7. The computer-implemented method of claim 1, wherein the first portion of information comprises information about one or more medications and the second portion of information comprises information about a diagnosis.

8. A non-transitory computer-readable medium, the non-transitory computer-readable medium comprising instructions for:
   training a first neural network autoencoder to encode information of a first type into a first vector representation, the first autoencoder comprising a first encoder that maps a first input vector to the first vector representation and a first decoder that maps the first vector representation to a first output vector, where the first decoder is trained to reduce the distance between the first output vector and the first input vector;
   training a second neural network autoencoder to encode information of a second type into a second vector representation, the second autoencoder comprising a second encoder that maps a second input vector to the second vector representation and a second decoder that maps the second vector representation to a second output vector, where the second decoder is trained to reduce the distance between the second output vector and the second input vector;
   providing a medical record of a past appointment of a patient;
   extracting from the medical record a first portion of information of the first type and a second portion of information of the second type;
   inputting the first portion of information to the first neural network autoencoder to output first encoded information;
   inputting the second portion of information to the second neural network autoencoder to output second encoded information;
   providing a database of clinical questions;
   inputting the first encoded information and second encoded information into a third neural network encoder to generate an aggregate encoding;
   predicting, by a question predictor, a clinical question to ask from the database of clinical questions based on the aggregate encoding.

9. The non-transitory computer-readable medium of claim 8, wherein the first neural network autoencoder is a variational autoencoder.

10. The non-transitory computer-readable medium of claim 8, wherein the first neural network autoencoder uses Kullback-Leibler divergence.

11. The non-transitory computer-readable medium of claim 8, wherein the second neural network autoencoder is a variational autoencoder.

12. The non-transitory computer-readable medium of claim 8, wherein the question predictor comprises a Q-learning system.

13. The non-transitory computer-readable medium of claim 8, wherein the question predictor comprises a Deep Q-learning system.

14. The non-transitory computer-readable medium of claim 8, wherein the first portion of information comprises information about one or more medications and the second portion of information comprises information about a diagnosis.

15. A computer-implemented method for generating questions for a clinical form, the method comprising:
   training a first neural network encoder to encode information of a first type into a first vector representation;
   training a second neural network encoder to encode information of a second type into a second vector representation;
   providing a medical record of a past appointment of a patient;
   extracting from the medical record a first portion of information of the first type and a second portion of information of the second type;
   inputting the first portion of information to the first neural network encoder to output first encoded information;
   inputting the second portion of information to the second neural network encoder to output second encoded information;

providing a database of clinical questions;

predicting, by a question predictor, a clinical question to ask from the database of clinical questions based on the first encoded information and second encoded information.

16. The computer-implemented method of claim 15, wherein the first neural network encoder is a variational autoencoder.

17. The computer-implemented method of claim 15, wherein the first neural network encoder uses Kullback-Leibler divergence.

18. The computer-implemented method of claim 15, wherein the second neural network encoder is a variational autoencoder.

19. The computer-implemented method of claim 15, wherein the question predictor comprises a Q-learning system.

20. The computer-implemented method of claim 15, wherein the question predictor comprises a Deep Q-learning system.

21. The computer-implemented method of claim 15, wherein the first portion of information comprises information about one or more medications and the second portion of information comprises information about a diagnosis.

22. A non-transitory computer-readable medium, the non-transitory computer-readable medium comprising instructions for:

training a first neural network encoder to encode information of a first type into a first vector representation;

training a second neural network encoder to encode information of a second type into a second vector representation;

providing a medical record of a past appointment of a patient;

extracting from the medical record a first portion of information of the first type and a second portion of information of the second type;

inputting the first portion of information to the first neural network encoder to output first encoded information;

inputting the second portion of information to the second neural network encoder to output second encoded information;

providing a database of clinical questions;

predicting, by a question predictor, a clinical question to ask from the database of clinical questions based on the first encoded information and second encoded information.

23. The non-transitory computer-readable medium of claim 22, wherein the first neural network encoder is a variational autoencoder.

24. The non-transitory computer-readable medium of claim 22, wherein the first neural network encoder uses Kullback-Leibler divergence.

25. The non-transitory computer-readable medium of claim 22, wherein the second neural network encoder is a variational autoencoder.

26. The non-transitory computer-readable medium of claim 22, wherein the question predictor comprises a Q-learning system.

27. The non-transitory computer-readable medium of claim 22, wherein the question predictor comprises a Deep Q-learning system.

28. The non-transitory computer-readable medium of claim 22, wherein the first portion of information comprises information about one or more medications and the second portion of information comprises information about a diagnosis.

* * * * *